United States Patent [19]

Riazi

[11] Patent Number: 5,215,461
[45] Date of Patent: Jun. 1, 1993

[54] ENDODONTIC APPLIANCE AND RELATED METHOD

[76] Inventor: John Riazi, 833 N. Portage Path, Akron, Ohio 44303

[21] Appl. No.: 673,945

[22] Filed: Mar. 22, 1991

[51] Int. Cl.$^5$ .......................... A61C 5/02; A61G 5/02
[52] U.S. Cl. ..................................... 433/224; 433/81; 433/102
[58] Field of Search .................. 433/102, 224, 81, 89, 433/90

[56] References Cited

U.S. PATENT DOCUMENTS

| | | | |
|---|---|---|---|
| 3,318,000 | 5/1967 | Paris | 433/224 |
| 3,466,752 | 9/1969 | Braun | 433/32 |
| 3,863,345 | 2/1975 | Malmin | 433/224 |
| 4,619,613 | 10/1986 | Fragan | 433/90 |
| 4,758,156 | 7/1988 | Johnson | 433/81 |
| 4,758,158 | 7/1988 | Pierce et al. | 433/90 |
| 4,863,072 | 9/1989 | Perler | 222/390 |
| 4,894,011 | 1/1990 | Johnson | 433/81 |
| 5,067,900 | 11/1991 | McSpadden | 433/81 |

OTHER PUBLICATIONS

"A New Gutta-Percha Technique"-Journal of Endodontics, vol. 4, No. 6, pp. 184-188, Jun., 1978.
"A Simple Standardized Technique for Filling Root Canals to the Dento-Cemental Junction with Perfect Fitting Impermeable Materials"—Oral Health, vol. 18, No. 11, pp. 577-584, Nov., 1928.

Primary Examiner—Cary E. O'Connor
Assistant Examiner—Cindy A. Cherichetti
Attorney, Agent, or Firm—Renner, Kenner, Greive, Bobak, Taylor & Weber

[57] ABSTRACT

An appliance (20) for use in conjunction with the obturation of prepared root canals employing a rigid carrier member (23) coated with a thermoplastic material (29) comprises an instrument (40) having a barrel (41), a movable plunger (43), and an orifice (48), and a quantity of the thermoplastic material (29) within the barrel. The orifice has a diameter greater than the distal end (30) of the rigid member, the member being insertable through the orifice and into the thermoplastic material whereby upon extrusion of a quantity of the thermoplastic material from the barrel, the rigid member is provided carrying a coating of thermoplastic material. The present invention also provides an appliance (60) for the obturation of prepared root canals comprising a rigid carrier member (62) having a distal end (68) insertable into a root canal and a diameter less than that of the canal; an instrument (61) having a barrel, (63) a movable plunger (65) and an orifice, (69) and a quantity of thermoplastic material (29) within the barrel; the orifice having a diameter greater than the distal end of the carrier member, the distal end being inserted through the orifice and into the thermoplastic material. whereupon extrusion therefrom, in response to movement of the plunger through the barrel toward the orifice, the carrier member is expelled carrying a coating of thermoplastic material covering at least the distal end for obturation of the canal. Finally, a method for coating a rigid carrier with thermoplastic material is provided.

15 Claims, 8 Drawing Sheets

ENDODONTIC APPLIANCE AND RELATED METHOD

TECHNICAL FIELD

The present invention relates in general to the field of endodontia. More particularly, the present invention relates to an appliance or tool for applying endodontic obturating material to a file which is, in turn, utilized in the obturation of a root canal. Use of the tool enables the practitioner to apply a uniform coating of obturating material onto the file in a facile and sterile manner. A method is also provided for coating an endodontic file with thermoplastic material to be employed in the obturation of a root canal.

BACKGROUND ART

In the traditional technique for obturating a root canal, strand-like pieces of a thermoplastic material, known as points, are inserted into a prepared or stripped root canal. Typically, gutta percha is employed as the point and these points are physically compacted by small manually actuated instruments known as "plungers" and "spreaders", or by machine driven "compactors". Another technique involves the use of a rigid carrier member that is coated with a thermoplastic material, such as gutta percha, inserted into the prepared root canal and then broken off, leaving a segment of the carrier and the coating within the root canal.

This procedure was first described in the Journal of Endodontics, Vol. 4, No. 6, pp. 184-88, June, 1978. It taught that a file can be utilized as the rigid carrier. The last file employed to instrument the canal is notched so that it will break away within the canal. It is then coated with sufficient gutta percha for obturation of the root canal, the gutta percha being heated sufficiently in an open flame to permit molding of the coating on the file with the fingers. The coated file is then inserted into the canal and broken off, as described hereinabove.

The author of this publication is also the patentee of several U.S. patents, including U.S. Pat. Nos. 4,758,156 and 4,894,011. While both are broadly directed toward the use of coated files, the elder patent features a rigid carrier tool that is provided with a distal end configuration that will resist rotation of the tool within the canal, thereby aiding breaking and removal of the proximal portion. Additionally, the shaft of the tool is provided with a reduced torque area to aid controlled breakage.

The latter patent further enhances the carrier member by providing a spiral groove along the distal portion to achieve the augering action, while resisting drilling. Rather significantly, the patent specifically states that the prior art teaching of a file as the carrier does have limitations which are overcome by the spiral groove construction.

Notwithstanding the usefulness of this technique for employing coated files and other rigid carrier tools, the foregoing patents and publication do not disclose any means for applying the coating other than manually and with heating over a flame. The present invention eliminates the need for manual manipulation, as well as any contact with the obturating material prior to placement within the root canal.

DISCLOSURE OF THE INVENTION

It is therefore an object of the present invention to provide an appliance for applying a uniform coating of thermoplastic material to a rigid carrier member, such as a file, for the obturation of root canals.

It is another object of the present invention to provide an appliance for applying a uniform coating of thermoplastic material to a rigid carrier member, in a facile and sterile manner.

It is yet another object of the present invention to provide an appliance for the obturation of prepared root canals which includes a rigid carrier member within a sealed instrument containing thermoplastic material.

It is yet another object of the present invention to provide a method for the obturation of prepared root canals in a sterile and facile manner.

At least one or more the foregoing objects, together with the advantages thereof over known methods and dental appliances, and which shall become apparent from the specification which follows, are accomplished by the invention as hereinafter described and claimed.

In general, the present invention provides an appliance for use in conjunction with the obturation of prepared root canals employing a rigid carrier member coated with a thermoplastic material which comprises an instrument having a barrel, a movable plunger and an orifice, and a quantity of thermoplastic material within the barrel; the orifice having a diameter greater than the distal end of the rigid member, the member being insertable through the orifice and into the thermoplastic material whereby upon extrusion of a quantity of the thermoplastic material from the barrel, the rigid member is provided carrying a coating of thermoplastic material.

The present invention also provides an appliance for the obturation of prepared root canals comprising a rigid carrier member having a distal end insertable into a root canal and a diameter less than that of the canal; an instrument having a barrel, a movable plunger and an orifice, and a quantity of thermoplastic material within the barrel; the orifice having a diameter greater than the distal end of the carrier member, the distal end being inserted through the orifice and into the thermoplastic material, whereupon extrusion therefrom, in response to movement of the plunger through the barrel toward the orifice, the carrier member is expelled carrying a coating of thermoplastic material covering at least the distal end for obturation of the canal.

The present invention also provides a method for coating a rigid carrier with thermoplastic material which comprises the steps of providing an instrument having a barrel, a movable plunger and an orifice, with a quantity of thermoplastic material; inserting the distal end of the rigid carrier through the orifice and into the thermoplastic material; and applying force to the plunger sufficient to extrude the carrier, carrying a coating of thermoplastic material thereon.

PREFERRED EMBODIMENT FOR CARRYING OUT THE INVENTION

Figure 12:
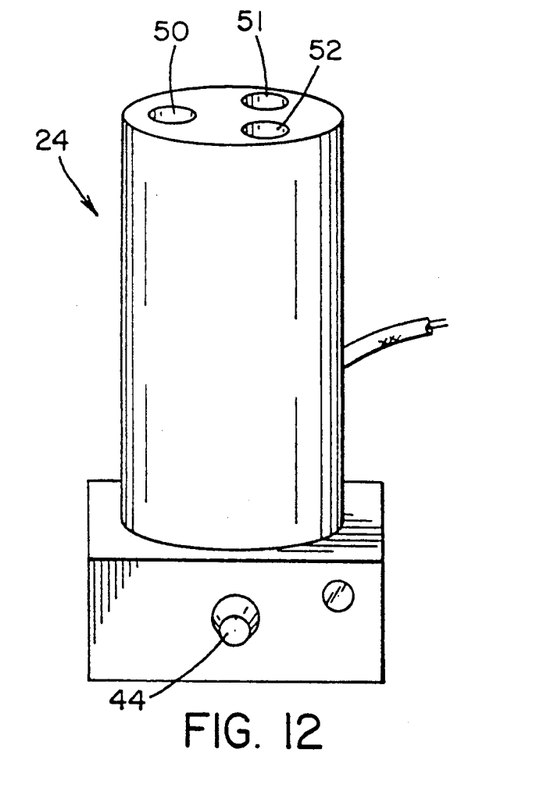
FIG. 12 is a perspective view of a conventional dental operatory heater, for the insertion of a plurality of syringes, according to the present invention.

With reference to the drawings, and in a particular FIGS. 1-4, the appliance employed for practice of the present invention is a syringe, referred to generally by the numeral 20. Obturating files 21 and 22 are also depicted as rigid carrier members which are employed with appliance 20 in one embodiment and as a component of an endodontic appliance, to be described hereinbelow. Finally, a dental operatory heater 23, or 24 (FIG. 12) can by employed, as will be explained hereinbelow.

Before proceeding with the description of the present inventions, it will be useful to describe briefly the technique for root canal obturation to which the inventions pertain. FIGS. 5-8 depict a tooth 25 in cross section having root canals 26 and 28 which have been prepared in the standard manner, including the use of files to remove the root and clean the canal. A file, such as 21 or 22, is provided with a quantity of a thermoplastic obturating material 29 such as gutta percha which can be molded onto the distal and medial portions of the file, 30 and 31 respectively, by hand or, the file can be precoated. In either event, to obturate the canal, the material 29 is first warmed over an open flame to the proper consistency.

Figures 5, 6:
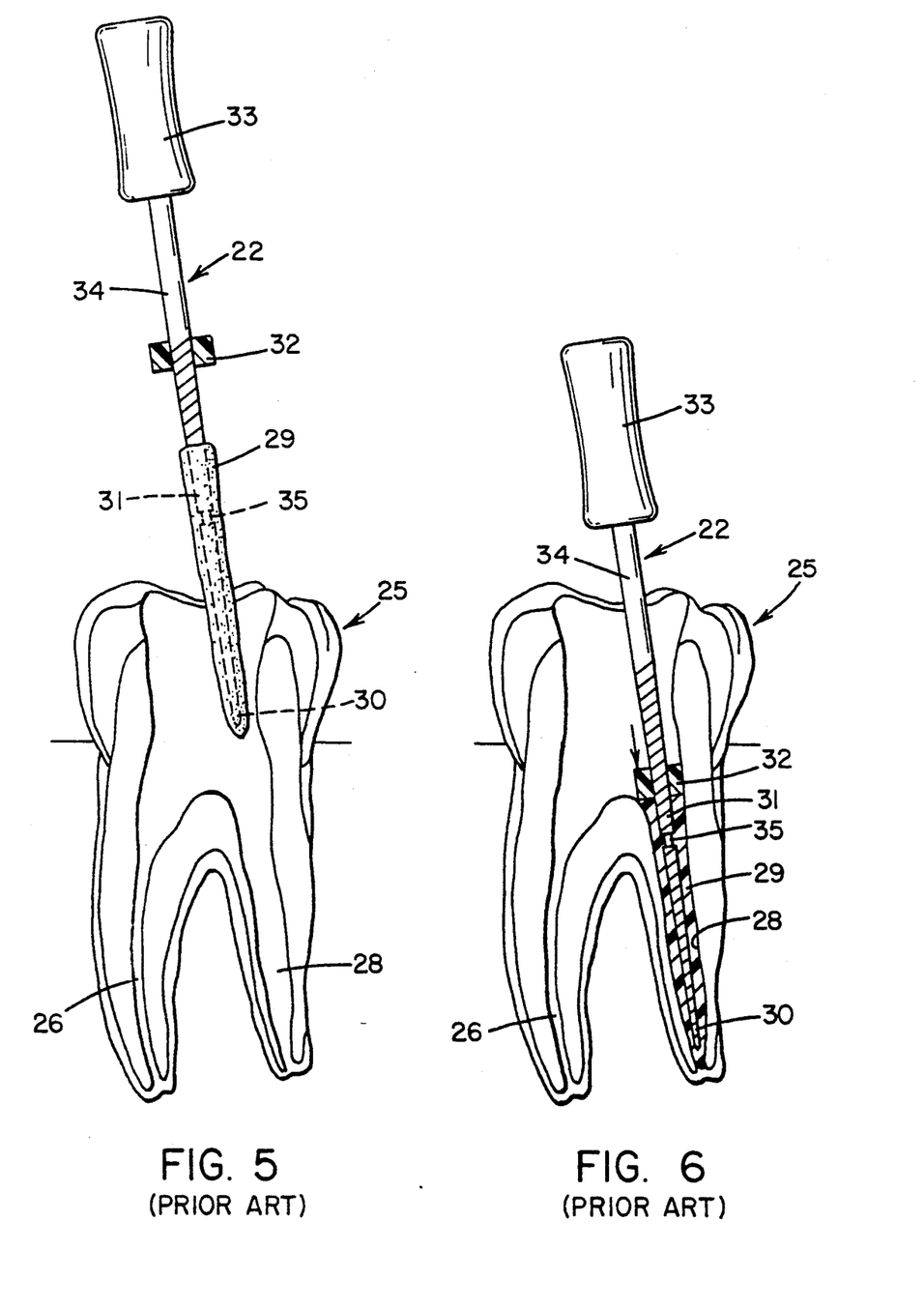
FIG. 5 is a further enlarged cross-sectional view of a tooth depicting stripped root canals and showing the insertion of an obturating tool, according to a technique of the prior art.
FIG. 6 is a cross-sectional view of a tooth depicting stripped root canals and showing the next sequence of applying obturating material into one canal, according to a technique of the prior art.
Figure 7:
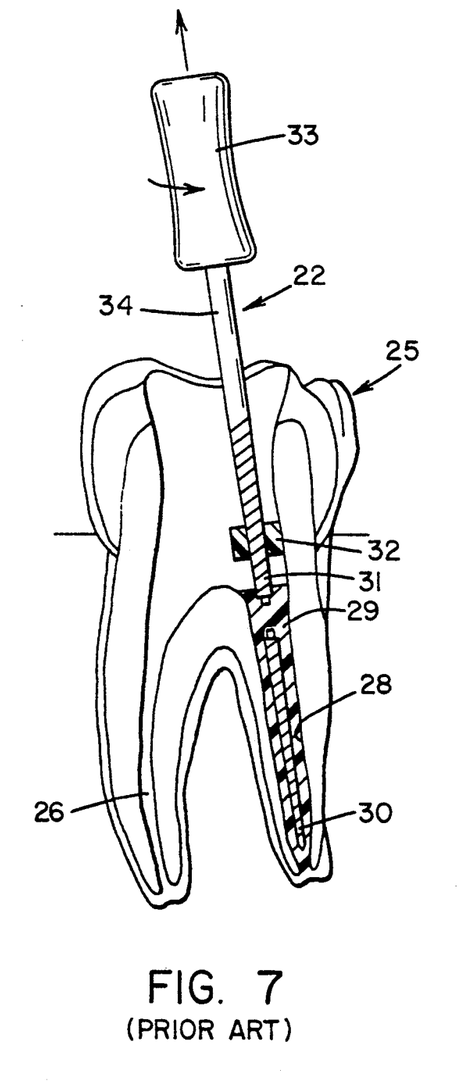
FIG. 7 is a cross-sectional view of a tooth depicting stripped root canals and showing the next sequence of rotating the obturating tool to sever the proximal portion from the distal portion within one canal, according to a technique of the prior art.
Figure 8:
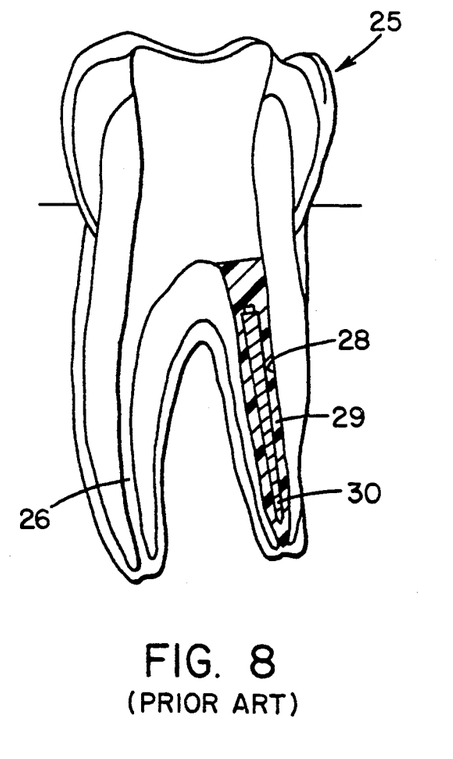
FIG. 8 is a cross-sectional view of a tooth depicting stripped root canals and showing the final sequence of removing the proximal portion of the obturating tool from one canal, according to a technique of the prior art.

The coated file is then inserted into canal 28, as depicted in FIGS. 5 and 6. In FIG. 6 a slidable washer 32 has been urged downwardly toward distal end 30, compacting the material 29 within the canal. Next, the file handle 33 is rotated and twisted, as depicted in FIG. 7 causing the proximal end 34 to sever from the distal end 30. To aid controlled breaking, the file 22 is provided a notch 35 by the practitioner after instrumenting the canal with an un-notched file 21 to determine the proper depth. Alternatively, the file can be purchased pre-notched from the manufacturer or supplier. Finally, in FIG. 8, the proximal end 34 of the tool 22 has been withdrawn, leaving the distal end 30 within the canal 28.

To this point, the technique described is well known in the prior art and is preferred by many practitioners. The present invention provides a novel appliance and related method for coating or providing coated files or other rigid carrier members. As noted hereinabove, a thermoplastic material is the accepted endodontic material for obturating root canals. A suitable thermoplastic material is selected from the group consisting of synthetic and natural trans 1,4-polyisoprene such as gutta percha, which is the cis-isomer of polyisoprone (natural rubber), or balata. While numerous fillers including barium sulfate, zinc oxide or titanium dioxide can be added as well as various plastizers, practice of the present invention is not limited to a specific composition.

Similarly, it is customary to heat the composition to a temperature at which it can flow under slight pressure which aids not only application of the material into the canal but also movement within the canal when the material is carefully compressed. Alternatively, it is possible to select a thermoplastic obturating material having a sufficiently high melt flow index to be flowable with less heating at lower temperatures. For a description of suitable thermoplastic obturating materials, see U.S. Pat. Nos. 4,632,977, 4,766,200, 4,882,407 and 4,966,952, the subject matter of which is incorporated herein by reference.

Figures 1, 2, 3, 4:
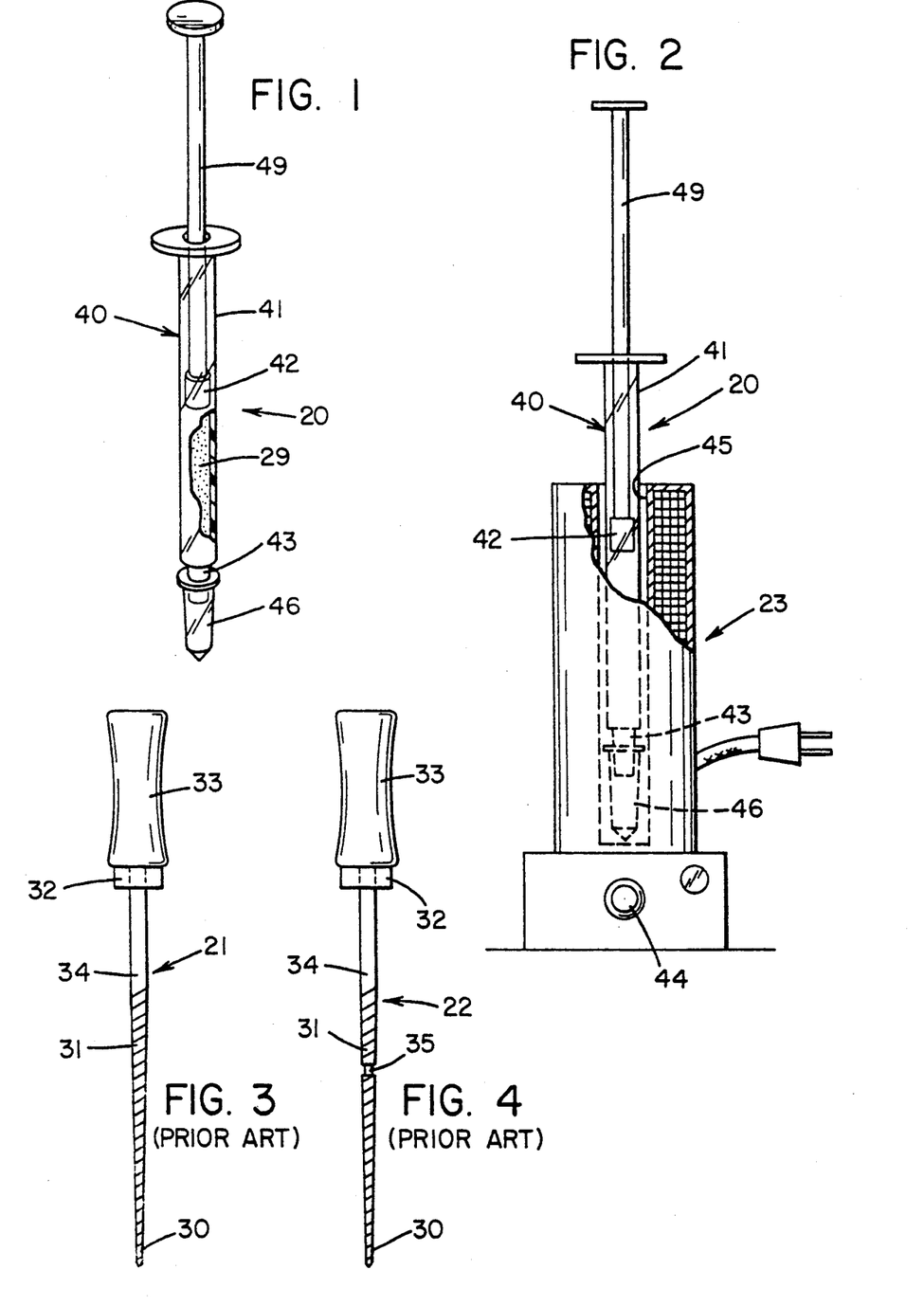
FIG. 1 is a perspective view of a syringe, providing thermoplastic obturating material, for practice of the present invention.
FIG. 2 is a side elevation of a conventional dental operatory heater, depicting the placement of a syringe for practice of the present invention.
FIG. 3 is an enlarged elevation of conventional endodontic file for use in conjunction with the present invention.
FIG. 4 is a side elevation of conventional endodontic file for use in conjunction with the present invention.

The appliance 20 depicted in the drawings comprises an instrument such as a commercially available, rigid plastic, disposable syringe 40, having a cylindrical barrel 41, a plunger 42, and ferrule 43. The appliance 20 is filled with a quantity of thermoplastic material 29, on the order of several cc's for a plurality of applications. In order to prepare the material for coating the file and subsequent obturation, the barrel is placed within a typical dental heater 23 which is preferably electrical and provides a rheostatic control 44 to adjust the heat. Ideally, the appliance 20 can be placed in the cavity 45 of the heater 23 to "warm" until use and can be sealed with a removable cap 46.

Figure 9:
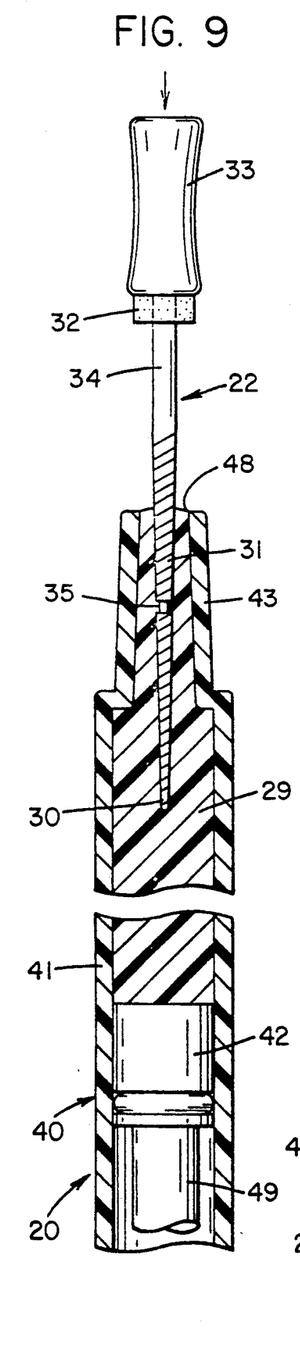
FIG. 9 is a side elevation, partially in section, depicting the insertion of an obturating file into the syringe, according to the present invention.
Figure 10:
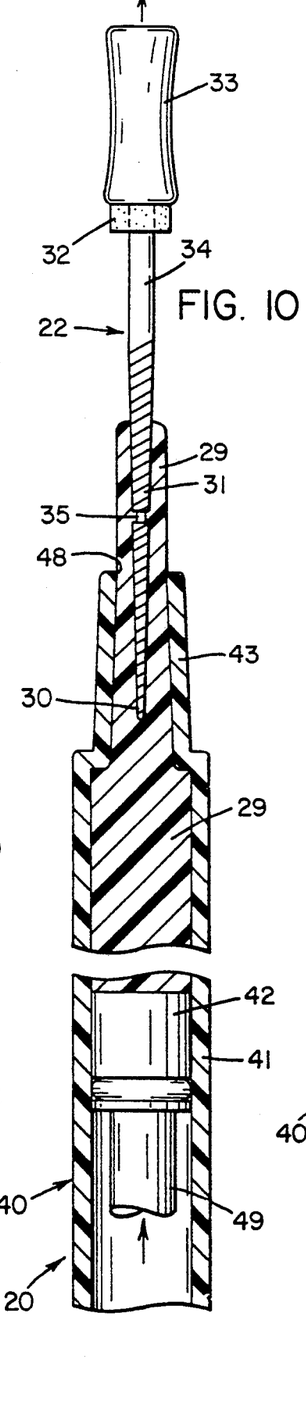
FIG. 10 is a side elevation, partially in section, depicting the extrusion of the obturating file and a coating of thermoplastic material from the syringe, according to the present invention.
Figure 11:
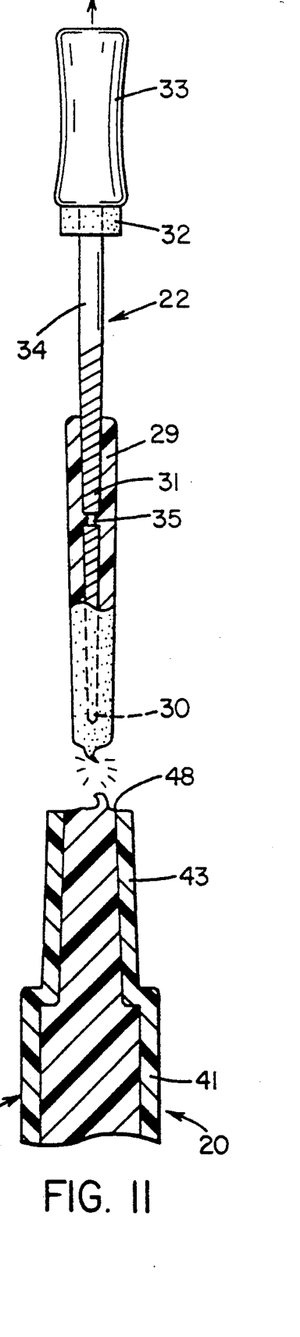
FIG. 11 is a side elevation, partially in section, depicting the removal of the coated obturating file from the syringe, according to the present invention.

With reference to FIGS. 9-11, the method for coating a file according to the present invention shall be described. After the appliance 20 and material 29 have been heated sufficiently to be extrudable from the ferrule 43, a file such as 22 that has been notched, is inserted through the opening 48 thereof and into the material, extending a distance into the barrel but not necessary to the plunger 42. Next by applying force to the plunger stem 49, plunger 42 urges a quantity of material out of the ferrule 43, carrying with it the file 22, as depicted in FIG. 10. Finally, as the distal end 30 of file 22 clears the opening 48, the file is received by grasping the handle 33 and is thereby provided with a uniform coating of material generally concentrically to all surfaces of the distal end and an area of the medial portion 31, depending upon the previous depth of insertion into the barrel 41. At this stage the coated file 22 is ready for the obturation of a root canal, 26 or 28, as described hereinabove.

Figure 13A:
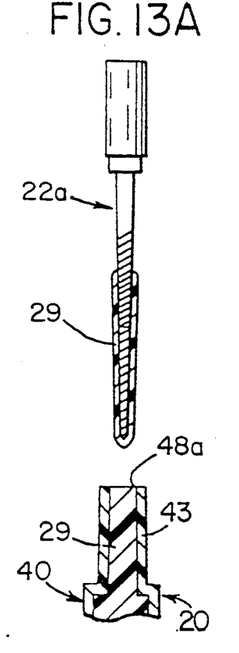
FIGS. 13A-C depict three obturating files carrying different thicknesses of obturating coating material, partially in section.
Figure 13B:
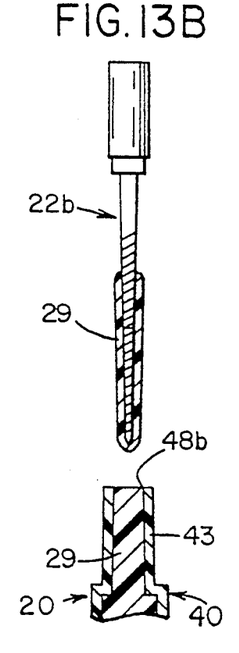
Figure 13C:
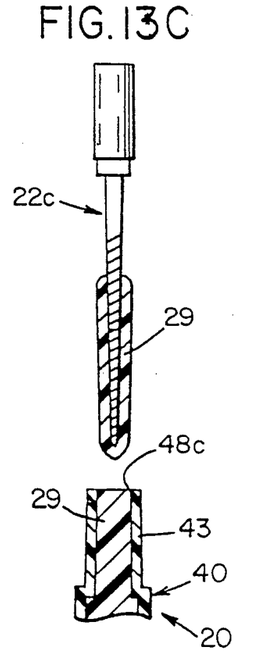

Because root canal sizes vary, the amount of material 29 carried by the file can be varied, as can the diameter of the files. With reference to FIGS. 13A-C, three files 22a, 22b and 22c are depicted. While each was originally the same the amount of material 29 applied thereto increases from 22a to 22c as a result of varying the diameter of opening 48a, 48b and 48c in ferrule 43 of appliance 20. To prepare three files concurrently, a heater 24 having three separate cavities 50-52 can be employed.

Figure 14A:
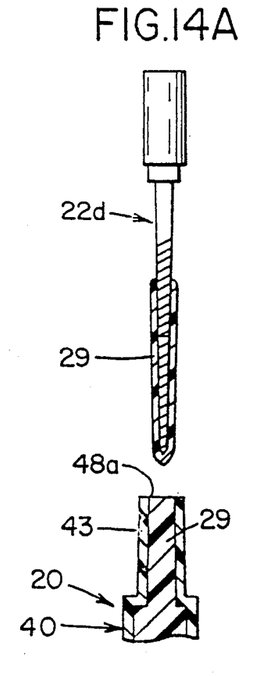
FIGS. 14A-C depict three obturating files of different sizes, carrying equal thicknesses of obturating coating material, partially in section.
Figure 14B:
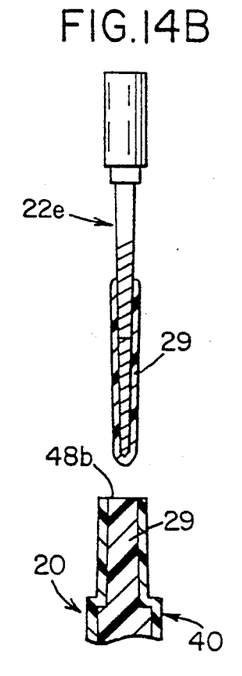
Figure 14C:
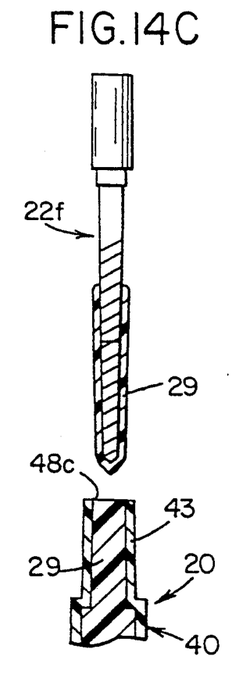

With reference to FIGS. 14A-C, three files 22d, 22e and 22f are depicted of increasing diameters. Each has been "extruded" from openings 48a, 48b, 48c, respectively, which results in generally uniform thicknesses of coatings. Of course, while not shown, the amount of material carried by the files 22d-22f could be varied by selecting ferrules (not shown) having different diameter openings.

Figure 15:
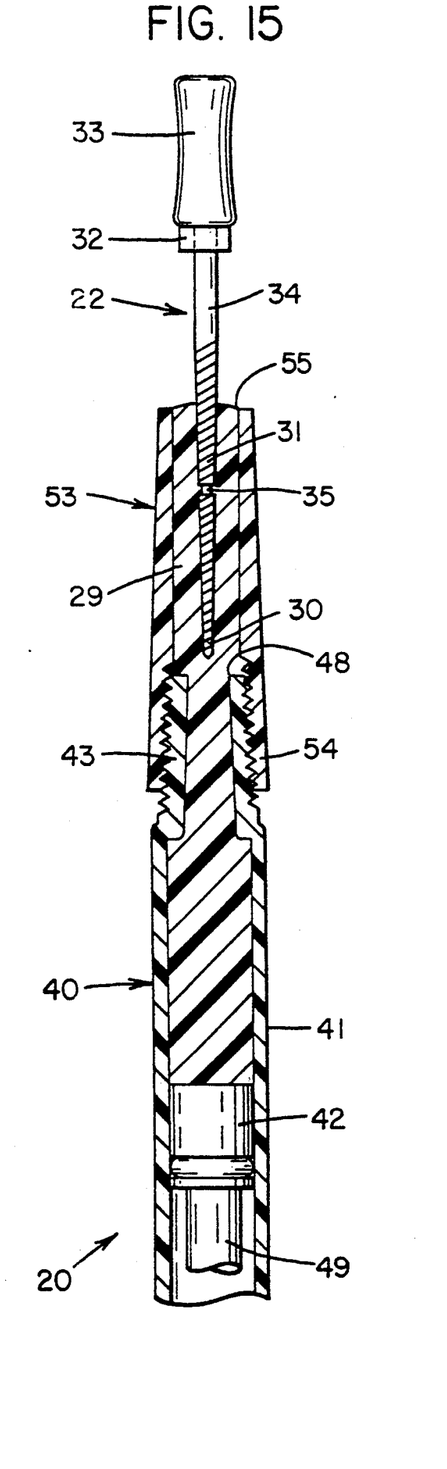
FIG. 15 is a side elevation, partially in section, depicting an alternate embodiment of the present invention for the coating of a file.

Alternatively, in FIG. 15 an accessory is depicted for applying greater amounts of material from one size of appliance 20. The accessory comprises an extension tube 53 having a base end 54, engageable with the exterior of ferrule 43. To aid attachment, the mating surfaces can be threaded which also allows the engagement to resist separation as the material 29 is driven into accessory 53. The function of accessory 53 is evident from the drawing which shows the diameter and the opening 55 being greater than that of the ferrule opening 48 so that a greater amount of material 29 can be applied to the file 22.

Figure 16:
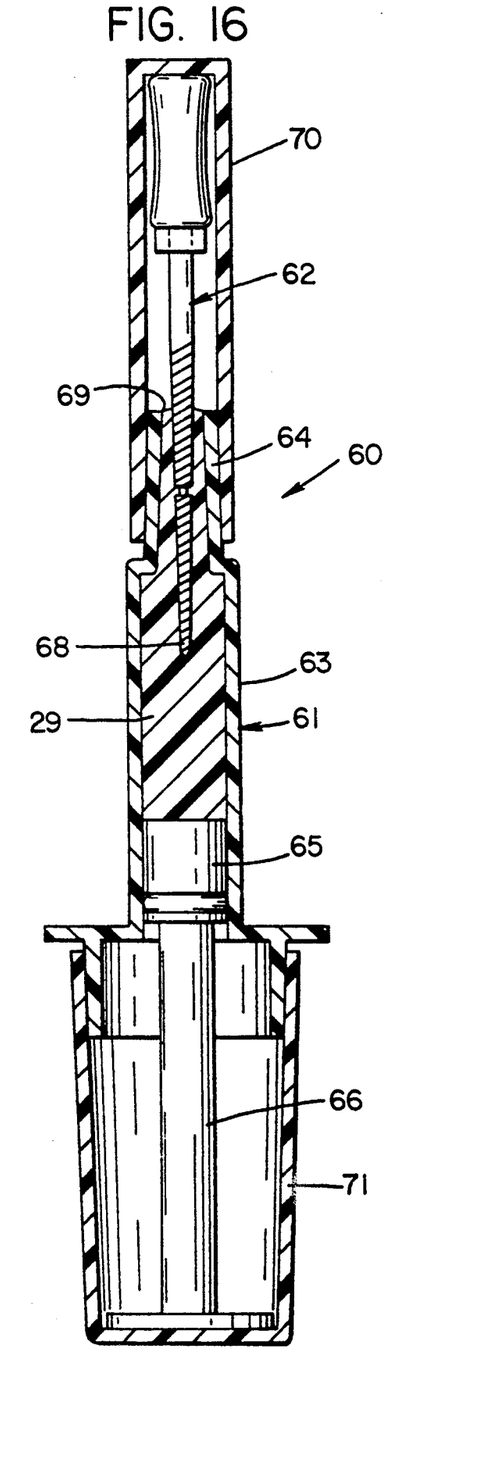
FIG. 16 is a side elevation, partially in section, depicting a further alternate embodiment of the present invention for the coating of a file.

A separate embodiment is depicted in FIG. 16 which comprises a single use appliance, with contained rigid carrier member, the combination being indicated generally by the numeral 60. Appliance 60 comprises a plunger assembly 61 and a file 62 provided therein. Plunger assembly, in turn, includes a barrel 63, ferrule 64, plunger 65, and plunger stem 66 and contains sufficient thermoplastic material 29 for coating the distal end 68 of a single file 62. The file 62 is inserted through an opening 69 of the ferrule 64 and into the material 29 and is capped with a removable cover 70, another cover 71 being provided over the plunger stem 66. Prior to use, the practitioner places the cover 70 and barrel 63 of appliance 60 into the cavity of the heater for several minutes prior to use. Then by removing the appliance and covers 70, 71, the file 62 can be "extruded" from the ferrule 64, as described hereinabove. The plunger assembly may then be discarded. It will be appreciated that appliance 60 can be provided in a variety of standard sizes, based upon the file size, and the file should be pre-notched. The appliance 60 provides a very sterile embodiment, because all components are sealed prior to actual use.

Figure 17:
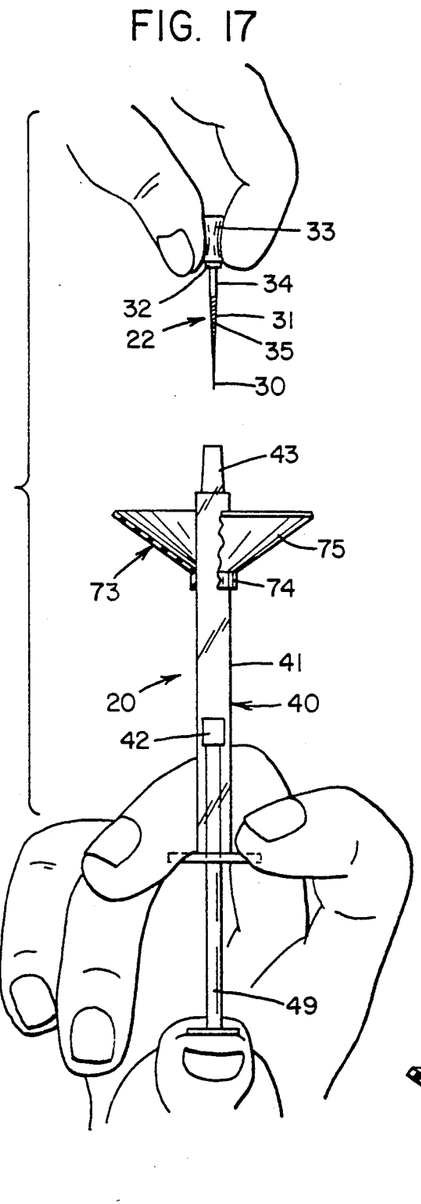
FIG. 17 is an elevation of the appliance of the present invention in use, depicting the use of an optional shield member.

In FIG. 17, the use of an optical shield 73, is depicted. Shield 73 is a cone-shaped member having a neck 74 adapted to slide over the barrel 41 of appliance 20. The body 75 provides an open hood surrounding the ferrule 43 which can "catch" the file 22 if it is misdirected toward the opening 48 during insertion. In this manner, the hand of the practitioner is protected from being pricked by the pointed end 30 of file 22. Of course, shield 73 can be employed as well with the appliance 60 and other variations of the present invention.

Figure 18:
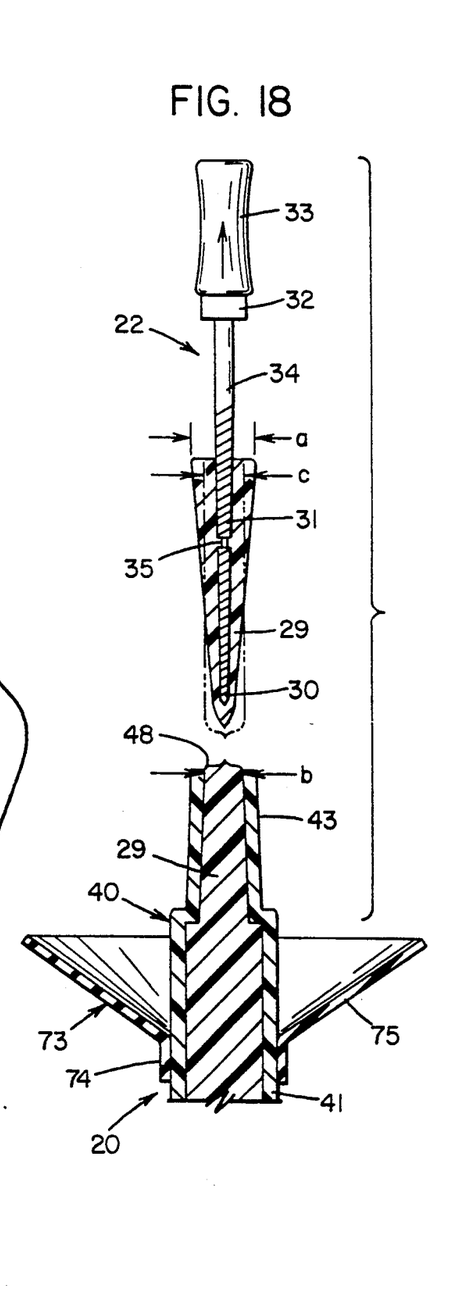
FIG. 18 is a, fragmentary, exploded view depicting a method for varying the coating thickness of thermoplastic material as it is applied to an obturating file.

Finally, an alternative method for coating files is discussed with reference to FIG. 18. In particular, it has been explained that as the file is extruded from the appliance 20, it receives a coating of thermoplastic material of thickness (c), based upon the diameter of opening 48 (b). However, if the rate of removal of the file is retarded by the receiving hand, a greater thickness (a) can be applied and similarly, if the withdrawal rate is increased by the receiving hand, a reduced thickness i.e., less than (c). In this manner, it is also possible to form tapered coatings, as depicted in FIG. 18.

Based upon the foregoing disclosure, it should now be apparent that the use of the appliances and method described herein will carry out the objects set forth hereinabove. It should also be apparent to those skilled in the art that the method of the present invention can be practiced with a variety of files or other rigid carrier members and appliances as disclosed herein to accommodate variations in root canal dimensions and the desire of the practitioner. Similarly, the present invention can be employed in conjunction with all types of obturating materials known to and employed by those skilled in the art.

It is, therefore, to be understood that any variations evident fall within the scope of the claimed invention and thus, the selection of specific thermoplastic materials, files or other carrier members can be determined without departing from the spirit of the invention herein disclosed and described. Moreover, the scope of the invention shall include all modifications and variations that may fall within the scope of the attached claims.

I claim:

1. A method for coating a rigid carrier with thermoplastic material comprising the steps of:
   providing an instrument having a barrel, a movable plunger, a ferrule carrying an orifice and extension means engageable with said ferrule having an opening, the diameter of which is different from the diameter of said orifice, with a quantity of thermoplastic material;
   inserting the distal end of said rigid carrier through said opening and into the thermoplastic material; and
   applying force to said plunger sufficient to extrude said rigid carrier, carrying a coating of thermoplastic material thereon.

2. A method, as set forth in claim 1, including the additional step of notching said rigid carrier a distance from the distal end commensurate with the depth of a prepared root canal.

3. A method, as set forth in claim 1, wherein said thermoplastic material is selected from the group consisting of synthetic and natural trans 1,4-polyisoprene.

4. A method, as set forth in claim 1, including the step of employing an endodontic file as said rigid carrier.

5. A method, as set forth in claim 1, including the additional step of heating said instrument and thermoplastic material prior to said step of applying force.

6. A method for coating a rigid carrier with thermoplastic material comprising the steps of:
   providing an instrument having a barrel, a movable plunger, and a ferrule carrying an orifice, with a quantity of thermoplastic material;

providing shield means engageable with said barrel and providing an open hood around said ferrule;

inserting the distal end of said rigid carrier through said orifice and into the thermoplastic material; and applying force to said plunger sufficient to extrude said rigid carrier, carrying a coating of thermoplastic material thereon.

7. A method, as set forth in claim 6, including the additional step of notching said rigid carrier a distance from the distal end commensurate with the depth of a prepared root canal.

8. A method, as set forth in claim 6, wherein said thermoplastic material is selected from the group consisting of synthetic and natural trans 1,4-polyisoprene.

9. A method, as set forth in claim 6, including the step of employing an endodontic file as said rigid carrier.

10. A method, as set forth in claim 6, including the additional step of heating said instrument and thermoplastic material prior to said step of applying force.

11. A method for coating a rigid carrier with thermoplastic material comprising the steps of:

providing an instrument having a barrel, a movable plunger, and an orifice with a quantity of thermoplastic material;

inserting the distal end of said rigid carrier through said orifice and into the thermoplastic material; and applying force to the plunger sufficient to extrude said rigid carrier, at a controlled rate, thereby applying a tapered coating of thermoplastic material to said rigid carrier.

12. A method, as set forth in claim 11, including the additional step of notching said rigid carrier a distance from the distal end commensurate with the depth of a prepared root canal.

13. A method, as set forth in claim 11, wherein said thermoplastic material is selected from the group consisting of synthetic and natural trans 1,4-polyisoprene.

14. A method, as set forth in claim 11, including the step of employing an endodontic file as said rigid carrier.

15. A method, as set forth in claim 11, including the additional step of heating said instrument and thermoplastic material prior to said step of applying force.

* * * * *